United States Patent [19]
Nordquist et al.

[11] Patent Number: 5,747,475
[45] Date of Patent: May 5, 1998

[54] CHITOSAN-DERIVED BIOMATERIALS

[75] Inventors: Robert E. Nordquist, Oklahoma City; Wei R. Chen, Norman; Raoul Carubelli; Robert Adams, both of Oklahoma City, all of Okla.

[73] Assignee: Wound Healing of Oklahoma, Oklahoma City, Okla.

[21] Appl. No.: 720,685

[22] Filed: Oct. 2, 1996

Related U.S. Application Data

[63] Continuation-in-part of Ser. No. 416,158, Apr. 4, 1995.

[51] Int. Cl.$^6$ .................... A61K 31/73; C08B 37/08
[52] U.S. Cl. ............................................. 514/55; 536/20
[58] Field of Search ............................ 514/55; 536/20

[56] References Cited

U.S. PATENT DOCUMENTS

| | | | |
|---|---|---|---|
| 4,473,652 | 9/1984 | Okazaki et al. | 436/536 |
| 4,615,878 | 10/1986 | Kass | 424/3 |
| 4,624,915 | 11/1986 | Schindler et al. | 435/4 |
| 4,873,092 | 10/1989 | Azuma et al. | 424/499 |
| 4,878,891 | 11/1989 | Judy et al. | 604/5 |
| 4,971,956 | 11/1990 | Suzuki et al. | 514/55 |
| 5,095,030 | 3/1992 | Levy et al. | 514/410 |
| 5,198,460 | 3/1993 | Pandey et al. | 514/410 |
| 5,214,036 | 5/1993 | Allison et al. | 514/185 |
| 5,238,810 | 8/1993 | Fujiwara et al. | 435/5 |
| 5,252,743 | 10/1993 | Barrett et al. | 548/303.7 |
| 5,258,453 | 11/1993 | Kopecek et al. | 525/54.1 |
| 5,266,302 | 11/1993 | Peyman et al. | 424/9 |
| 5,283,255 | 2/1994 | Levy et al. | 514/410 |
| 5,314,905 | 5/1994 | Pandey et al. | 514/410 |
| 5,451,237 | 9/1995 | Vehige | 8/507 |
| 5,576,013 | 11/1996 | Williams et al. | 424/423 |

FOREIGN PATENT DOCUMENTS

WO 94/15583   7/1994   WIPO.

OTHER PUBLICATIONS

Vaccine, Mar. 1984, vol. 2, No. 1, pp. 93–99, XP002017431, Nishimura K. et al.: "Immunological activity of chitin and its derivatives."

Vaccine, Dec. 1985, vol. 3, No. 5, pp. 379–384, XP002017432, Nishimura K. et al.: "Adjuvant activity of chitin derivatives in mice and guines–pigs".

J. Control. Release, Mar. 1994, vol. 29, No. 3, pp. 329–338, XP002017433, Luessen H.L. et al: "Bioadhesive polymers for the peroral delivery of peptide drugs".

Lasers in Medical Science, vol. 8, No. 3, 1 Sep. 1993, pp. 185–196, XP000575069 Folck S. T. et al: "Thermal damage of blood vessels in a rat skin–flap window chamber using indocyanine green and a pulsed alexandrite laser: a feasibility study".

Proceedings of the IEEE, vol. 80, No. 6, 1 Jun. 1992, pp. 869–889, XP0000311053, Marcus S.L.: "Photodynamic therapy of human cancer".

Lasers in Surgery and Medicine, vol. 15, No. 4, 1 Jan. 1994, pp. 342–350, XP000484642, Zhengang Yang et al.: "Tumor cell–enchanced sensitivity of vascular endothelial cells to photodynamic therapy".

Seminars in Hematology, vol. 26, No. 2, 1 Apr. 1989, pp. 157–173, XP000501369 Kreimer–Birnbaum M.: "Modified prophyrins, chlorins, phtalocyanines, and purpurins: second-–generation photosensitizers for photodynamic therapy".

Database WPI, Section CH, Week 9421, Derwent Publications Ltd., London, GB; Class B04, AN 94–170527, XP00002017434 & JP 06 109 731 A (Ibiden Co Ltd), 22 Apr. 1994.

Patent Abstracts of Japan, vol. 18, No. 384 (P–1772), 19 Jul. 1994.

*Photodynamic Therapy and Biomedical Lasers*, Experta Medica, P. Spinelli, M. Dal Fanmte, R. Marchesini, 1992, Table of Contents and pp. 513–520 and 698–701.

*Photodynamic Therapy—Coming of Age*, Barbara W. Henderson, Photodermatology, 1989, pp. 200–211.

Primary Examiner—Kathleen K. Fonda
Attorney, Agent, or Firm—Fellers, Snider, Blankenship, Bailey & Tippens

[57] ABSTRACT

Chitosan-derived biomaterials, and, more specifically, chitosan modified by the addition of a monosaccharide or oligosaccharide side chain to its free amino groups. The modified chitosan ("glycated chitosan") is preferably stabilized by reduction. In one particularly preferred embodiment, a galactose derivative of chitosan ("galactochitosan") is provided. The chitosan-derived biomaterials are useful in a myriad of biomedical applications, including as an immunoadjuvant in laser/sensitizer assisted immunotherapy.

19 Claims, 5 Drawing Sheets

CHITOSAN-DERIVED BIOMATERIALS

CROSS REFERENCE TO RELATED APPLICATION

This application is a continuation-in-part of copending U.S. patent application Ser. No. 08/416,158, filed Apr. 4, 1995.

BACKGROUND OF THE INVENTION

TECHNICAL FIELD

The present invention relates generally to methods for treating neoplasms and other medical disorders and, more specifically, to chitosan-derived biomaterials used in connection with such methods. The utility and efficacy of the chitosan-derived biomaterials is well illustrated in a novel cancer treatment which combines photodynamic therapy and tumor immunotherapy to induce neoplastic cellular destruction and to stimulate the self-immunological defense system against residual neoplastic cells.

BACKGROUND

Chitosan is a derivative of chitin, a compound usually isolated from the shells of some crustaceans such as crab, lobster and shrimp. Chitin is a linear homopolymer composed of N-acetylglucosamine units joined by $\beta$ 0→4 glycosidic bonds. Chitin, chitosan (partially deacetylated chitin) and their derivatives are endowed with interesting chemical and biological properties that have led to a varied and expanding number of industrial and medical applications.

A neoplasm is an abnormal tissue that grows by cellular proliferation more rapidly than normal. It continues to grow even after the stimulus that initiated its growth dissipates. Neoplasms show a partial or complete lack of structural organization and functional coordination with the normal tissue and usually form a distinct mass which may be either benign or malignant.

Cancer is a general term frequently used to indicate any of the various types of malignant neoplasms, most of which invade surrounding tissues, may metastasize to several sites, and are likely to recur after attempted removal and to cause death of the patient unless adequately treated. Cancer can develop in any tissue of any organ at any age.

Once an unequivocal diagnosis of cancer is made, treatment decisions become paramount. Though no single treatment approach is applicable to all cancers, successful therapy must be focused on the primary tumor and its metastases, whether clinically apparent or microscopic.

CONVENTIONAL TREATMENTS

Historically, local and regional therapy, such as surgery or radiation, have been used in cancer treatment, along with systemic therapy, e.g., drugs.

Surgery is the oldest effective form of cancer therapy. In 1988, about 1,500,000 persons developed cancer; of those, about 515,000 had cancer of either the skin or cervix. About 985,000 had other systemic forms; 64% had operable lesions, with an estimated cure rate of 62%. Cancers that may be positively influenced with surgery alone, if detected in early stages, include those of the cervix, breast, bladder, colon, prostate, larynx, endometrium, ovary, oral cavity, kidney, testis (nonsemino-matous) and lung (non-small cell). It must be noted, however, that the percentage rate of treatment success varies greatly between the cancer sites.

Radiation plays a key role in the remediation of Hodgkin's disease, nodular and diffuse non-Hodgkin's lymphomas, squamous cell carcinoma of the head and neck, mediastinal germ-cell tumors, seminoma, prostate cancer, early stage breast cancer, early stage non-small cell lung cancer, and medulloblastoma. Radiation can be used as palliative therapy in prostate cancer and breast cancer when bone metastases are present, in multiple myeloma, advanced stage lung and esophagopharyngeal cancer, gastric cancer, and sarcomas, and in brain metastases. Cancers that may be curable with radiation alone include Hodgkin's disease, early-stage non-Hodgkin's lymphomas, cancers of the testis (seminomal), prostate, larynx, cervix, and, to a lesser extent, cancers of the nasopharynx, nasal sinuses, breast, esophagus, and lung.

Antineoplastic drugs are those that prevent cell division (mitosis), development, maturation, or spread of neoplastic cells. The ideal antineoplastic drug would destroy cancer cells without adverse effects or toxicities on normal cells, but no such drug exists. Despite the narrow therapeutic index of many drugs, however, treatment and even cure are possible in some patients. Certain stages of choriocarcinoma, Hodgkin's disease, diffuse large cell lymphoma, Burkitt's lymphoma and leukemia have been found to be susceptible to antineoplastics, as have been cancers of the testis (nonseminomatous) and lung (small cell). Common classes of antineoplastic drugs include alkylating agents, antimetabolites, plant alkaloids, antibiotics, nitrosoureas, inorganic ions, enzymes, and hormones.

Despite some success, the above treatments are not effective to the degree desired, and the search has continued for more efficacious therapies.

RECENT ADVANCES

Two of the more recent oncological treatment modalities investigated by the medical community are photodynamic therapy and tumor immunotherapy.

I. PHOTODYNAMIC THERAPY

It has been known for many years that photosensitizing compounds show a photochemical reaction when exposed to light. Photodynamic therapy (PDT) uses such photosensitizing compounds and lasers to produce tumor necrosis. Treatment of solid tumors by PDT usually involves the systemic administration of tumor localizing photosensitizing compounds and their subsequent activation by laser. Upon absorbing light of the appropriate wavelength the sensitizer is converted from a stable atomic structure to an excited state. Cytotoxicity and eventual tumor destruction are mediated by the interaction between the sensitizer and molecular oxygen within the treated tissue to generate cytotoxic singlet oxygen.

Two good general references pertaining to PDT, biomedical lasers and photosensitizing compounds, including light delivery and dosage parameters, are *Photosensitizing Compounds: Their Chemistry, Biology and Clinical Use*, published in 1989 by John Wiley and Sons Ltd., Chichester, U.K., ISBN 0 471 92308 7, and *Photodynamic Therapy and Biomedical Lasers: Proceedings of the International Conference on Photodynamic Therapy and Medical Laser Applications, Milan, 24–27 Jun. 1992*, published by Elsevier Science Publishers B.V., Amsterdam, The Netherlands, ISBN 0 444 81430 2, both incorporated herein by reference.

United States patents related to PDT include U.S. Pat. Nos. 5,095,030 and 5,283,225 to Levy et al.; U.S. Pat. No. 5,314,905 to Pandey et al.; U.S. Pat. No. 5,214,036 to Allison et al; and U.S. Pat. No. 5,258,453 to Kopecek et al., all of which are incorporated herein by reference. The Levy patents disclose the use of photosensitizers affected by a wavelength of between 670–780 nm conjugated to tumor specific antibodies, such as receptor-specific ligands, immunoglobulins or immunospecific portions of immunoglobulins. The Pandey patents are directed to pyropheophorbide compounds for use in standard photodynamic therapy. Pandey also discloses conjugating his compositions with ligands and antibodies. The Allison patent is similar to the Levy patents in that green porphyrins are conjugated to lipocomplexes to increase the specificity of the porphyrin compounds for the targeted tumor cells. The Kopecek patent also discloses compositions for treating cancerous tissues. These compositions consist of two drugs, an anti-cancer drug and a photoactivatable drug, attached to a copolymeric carrier. The compositions enter targeted cells by pinocytosis. The anti-cancer drug acts after the targeted cell has been invaded. After a period of time, a light source is used to activate the photosensitized substituent.

II. TUMOR IMMUNOTHERAPY

The major functions of the immune system are to develop the concept of "self" and eliminate what is "nonself". Although microorganisms are the principal nonself entities encountered every day, the immune system also works to eliminate neoplasms and transplants. See Chapters 18 and 103 of *The Merck Manual of Diagnosis and Therapy*, Sixteenth Edition, published in 1992 by Merck Research Laboratories of Rahway, N. J., ISBN 0911910-16-6 and 0076-6526; the same being incorporated herein by reference.

There are several distinct types of immunity. Nonspecific, or innate, immunity refers to the inherent resistance manifested by a species that has not been immunized (sensitized or allergized) by previous infection or vaccination. Its major cellular component is the phagocytic system, whose function is to ingest and digest invading microorganisms. Phagocytes include neutrophils and monocytes in the blood and macrophages in the tissues. Complement proteins are the major soluble component of nonspecific immunity. Acute phase reactants and cytokines, such as interferon, are also part of innate immunity.

Specific immunity is an immune status in which there is an altered reactivity directed solely against the antigenic determinants (infectious agent or other) that stimulated it. It is sometimes referred to as acquired immunity. It may be active and specific, as a result of naturally acquired (apparent or inapparent) infection or intentional vaccination; or it may be passive, being acquired from a transfer of antibodies from another person or animal. Specific immunity has the hallmarks of learning, adaptability, and memory. The cellular component is the lymphocyte (e.g., T-cells, B-cells, natural killer (NK) cells), and immunoglobulins are the soluble component.

The action of T-cells and NK-cells in recognizing and destroying parasitized or foreign cells is termed cell-mediated immunity. In contradistinction to cell-mediated immunity, humoral immunity is associated with circulating antibodies produced, after a complex recognition process, by B-cells.

As regards tumor immunology, the importance of lymphoid cells in tumor immunity has been repeatedly shown. A cell-mediated host response to tumors includes the concept of immunologic surveillance, by which cellular mechanisms associated with cell-mediated immunity destroy newly transformed tumor cells after recognizing tumor-associated antigens (antigens associated with tumor cells that are not apparent on normal cells). This is analogous to the process of rejection of transplanted tissues from a nonidentical donor. In humans, the growth of tumor nodules has been inhibited in vivo by mixing suspensions of a patient's peripheral blood lymphocytes and of tumor cells, suggesting a cell-mediated reaction to the tumor. In vitro studies have shown that lymphoid cells from patients with certain neoplasms show cytotoxicity against corresponding human tumor cells in culture. These cytotoxic cells, which are generally T-cells, have been found with neuroblastoma, malignant melanomas, sarcomas, and carcinomas of the colon, breast, cervix, endometrium, ovary, testis, nasopharynx, and kidney. Macrophages may also be involved in the cell-mediated host's response to tumors when in the presence of tumor-associated antigens, lymphokines or interferon.

Humoral antibodies that react with tumor cells in vitro have been produced in response to a variety of animal tumors induced by chemical carcinogens or viruses. Hydridoma technology in vitro permits the detection and production of monoclonal antitumor antibodies directed against a variety of animal and human neoplasms. Antibody-mediated protection against tumor growth in vivo, however, has been demonstrable only in certain animal leukemias and lymphomas. By contrast, lymphoid cell-mediated protection in vivo occurs in a broad variety of animal tumor systems.

Immunotherapy for cancer is best thought of as part of a broader subject, namely biologic therapy, or the administration of biologic-response modifiers. These agents act through one or more of a variety of mechanisms (1) to stimulate the host's antitumor response by increasing the number of effector cells or producing one or more soluble mediators; (2) to serve as an effector or mediator; (3) to decrease host suppressor mechanisms; (4) to alter tumor cells to increase their immunogenicity or make them more likely to be damaged by immunologic processes; or (5) to improve the host's tolerance to cytotoxics or radiation therapy. Heretofore the focus of cell-mediated tumor immunotherapy has been on reinfusion of the patient's lymphocytes after expansion in vitro by exposure to interleukin-2. One variation includes isolating and expanding populations of lymphocytes that have infiltrated tumors in vivo, so-called tumor-infiltrating lymphocytes. Another is the concurrent use of interferon, which is thought to enhance the expression of histocompatibility antigens and tumor-associated antigens on tumor cells, thereby augmenting the killing of tumor cells by the infused effector cells.

Humoral therapy, on the other hand, has long concentrated on the use of antitumor antibodies as a form of passive immunotherapy, in contrast to active stimulation of the host's own immune system. Another variation is the conjugation of monoclonal antitumor antibodies with toxins, such as ricin or diphtheria, or with radioisotopes, so the antibodies will deliver these toxic agents specifically to the tumor cells. Active immunization with a host's own tumor cells, after irradiation, neuraminidase treatment, hapten conjugation, or hybridization has also been tried. Clinical improvement has been seen in a minority of patients so treated. Tumor cells from others have been used after their irradiation in conjunction with adjuvants in acute lymphoblastic leukemia and acute myeloblastic leukemia after remission. Prolongation of remissions or improved reinduction rates have been reported in some series, but not in most. Interferons, tumor necrosis factor and lymphotoxins have also been used to affect immunologically mediated mechanisms. A recent approach, using both cellular and humoral mechanisms, is the development of "heterocross-linked antibodies," including one antibody reacting with the tumor cell linked to a second antibody reacting with a cytotoxic effector cell, making the latter more specifically targeted to the tumor. Host immune cell infiltration into a PDT treated murine tumor has been reported.

COMBINED PDT AND IMMUNOTHERAPY

The potential for combining PDT with immunotherapy was explored by Krobelik, Krosl, Dougherty and Chaplin. See *Photodynamic Therapy and Biomedical Lasers*, supra, at pp. 518–520. In their study, they investigated a possibility of amplification of an immune reaction to PDT and its direction towards more pervasive destruction of treated tumors. The tumor, a squamous cell carcinoma SCCVII, was grown on female C3H mice. An immunoactivating agent SPG (a high molecular weight B-glucan that stimulates macrophages and lymphoid cells to become much more responsive to stimuli from cytokines and other immune signals) was administered intramuscularly in 7 daily doses either ending one day before PDT or commencing immediately after PDT. Photofrin based PDT was employed; photofrin having been administered intravenously 24 hours before the light treatment. The SPG immunotherapy was shown to enhance the direct killing effect of the PDT. The indirect killing effect (seen as a decrease in survival of tumor cells left in situ) was, however, much more pronounced in tumors of animal not receiving SPG. The difference in the effectiveness of SPG immunotherapy when performed before and after PDT suggested that maximal interaction is achieved when immune activation peaks at the time of the light delivery or immediately thereafter. With SPG starting after PDT (and attaining an optimal immune activation 5–7 days later), it is evidently too late for a beneficial reaction.

In another study the use of PDT to potentiate the effect of bioreactive drugs that are cytotoxic under hypoxic conditions was investigated. See *Photodynamic Therapy and Biomedical Lasers*, supra, at pp. 698–701. It was found that the antitumor activity of such drugs can be enhanced in vivo when they are used in combination with treatments that increase tumor hypoxia.

OBJECT

It is an object of this invention to improve the treatment of neoplasms and other medical disorders. This is accomplished through the use of novel chitosan-derived biomaterials. In one treatment, the chitosan-derived biomaterials are used in a combined photodynamic and immunologic therapy in such a way as to cause immediate neoplastic cellular destruction while concomitantly stimulating the self-immunological defense system against proliferation of residual or metastatic neoplastic cells.

SUMMARY OF THE INVENTION

The present invention encompasses chitosan-derived biomaterials, and, more specifically, chitosan modified by the addition of a monosaccharide or oligosaccharide side chain to its free amino groups. The modified chitosan ("glycated chitosan") is preferably stabilized by reduction.

In one particularly preferred embodiment, a galactose derivative of chitosan ("galacto-chitosan") is provided.

The chitosan-derived biomaterials are useful in a myriad of applications, including as an immunoadjuvant or as a component of an immunoadjuvant, as described in detail herein. Though the majority of the disclosure hereinabove and hereunder focuses on the use of glycated chitosan in connection with laser/sensitizer assisted immunotherapy, the subject of the copending application cross-referenced above and incorporated by reference herein, it is important to note that there exist other potentially significant uses of the chitosan-derived biomaterials disclosed and claimed herein. Some of these alternative uses, which may or may not related to the treatment of neoplasms, are detailed infra.

Notwithstanding other uses, a principal use of the chitosan-derived biomaterials is as an immunoadjuvant in connection with what has been called laser/sensitizer assisted immunotherapy, and it is in this context that the chitosan-derived biomaterials are described in detail.

Laser/sensitizer assisted immunotherapy utilizing the present invention encompasses introducing into a neoplasm (1) a chromophore and (2) an immunoadjuvant comprising chitosan-derived biomaterials. The neoplasm is then lased at an irradiance sufficient to induce neoplastic cellular destruction and to stimulate cell-mediated and humoral immune responses.

In accordance with one aspect of the invention, a neoplasm, such as a malignant tumor, is injected with a solution containing a chromophore and a chitosan-derived immunoadjuvant. A low energy laser emitting a wavelength of radiation complementary to that of the chromophore is then focused on the neoplasm for a duration sufficient to elevate the temperature of the neoplasm to a level that induces neoplastic cellular destruction and stimulates the self-immunological defense system against neoplastic cellular multiplication. A number of alternative chromophores and immunoadjuvants are provided, along with irradiance parameters.

In accordance with another aspect of the invention, a solution of indocyanine green (ICG) and glycated chitosan is prepared at a concentration of 0.1 to 2% of ICG to chitosan. The solution is injected into the neoplasm at a dosage of 70 to 400 μl. The neoplasm is then lased using a laser having a power of about 5 watts and a wavelength of radiation capable of readily penetrating normal cellular tissues without significant disruption. The irradiation continues for a duration of 1 to 10 minutes, which is sufficient to elevate the temperature of the neoplasm to a level that induces neoplastic cellular destruction and stimulates cell-mediated and humoral immune responses.

The present invention has several advantages over other conventional and unconventional treatment modalities. The combination of sensitizer and immune-stimulation adjuvant is the key. The most significant advantage is a combined acute and chronic tumor destruction. The acute tumor loss is caused by photovaporization, photoablation or thermal killing of the neoplastic tissue, on a large and controlled scale, in the immediate area, reducing the tumor burden and hence the base of multiplication so that the self-defense system can fight a weaker enemy. When photothermal destruction occurs, the fragmented tissue and cellular molecules are disbursed within the host in the presence of the immunologically potentiating material, such as chitosan. In effect, an in situ vaccine is formed. This mixture of materials then circulates in the host and is detected by the immunological surveillance system. There follows an immediate mobilization of cell-mediated immunity which encompasses NK-cells and recruited killer T-cells. These cells migrate to the sites of similar antigens or chemicals. In time, the cell-mediated immunity shifts to a humoral immunity with the production of cytotoxic antibodies. These antibodies freely circulate about the body and attach to cells and materials for which they have been encoded. If this attachment occurs in the presence of complement factors, the result is cellular death. The time frames for these two immunologic modes of action are 0 to 2 weeks for the cell-mediated response, while the humoral arm matures at approximately 30 days and should persist for long periods, up to the life span of the host.

As the wavelength of radiation used is not readily absorbed by normal cellular tissues, collateral damage is reduced to a tolerable level. Particularly when the laser power is carefully chosen under a certain damage threshold, the laser will do little damage to tissue in the path of the leaser beam, such as skin. This characteristic makes a non-invasive treatment possible. Even in the case where diseased tissues are deep inside the body, an endoscope and fiber optics can easily reach the treatment site.

A chromophore of a complementary absorption wavelength makes the laser treatment highly selective. Only the chromophore injected area sustains noticeable tissue damage. The concentration of chromophore, the dosage of chromophore and immunoadjuvant, and the timing of administration allow for temporal and spatial control of the induced photothermal effect. The optimal administration can be achieved by considering the physical and chemical characteristics of the chromophore and by considering the tissue responses to the photothermal interaction. Equally important are the natural reactions between the chromophore and its host tissues without any laser stimulation, such as the molecules breaking down over time, as well as the migration of molecules through the circulatory and excretory systems. The preferred chromophore of the present invention, ICG, is non-toxic and can be easily excreted in a short period through the liver and kidney.

In sum, long term survival with total cancer eradication can be achieved by the present invention. It is a combined result of reduced tumor burden due to photothermal interactions and an enhanced immune system response due to the presence of chitosan or other immunomodulators.

Still other objects and advantages of the present invention will become readily apparent to those skilled in this art from the following detailed description, wherein there is shown and described only the preferred embodiments of the invention, simply by way of illustration of the best mode contemplated for carrying out the invention. As will be realized, the invention is capable of modifications in various obvious respects, all without departing from the invention. Accordingly, the description should be regarded as illustrative in nature, and not as restrictive.

DETAILED DESCRIPTION OF THE PREFERRED EMBODIMENTS

Figure 1:
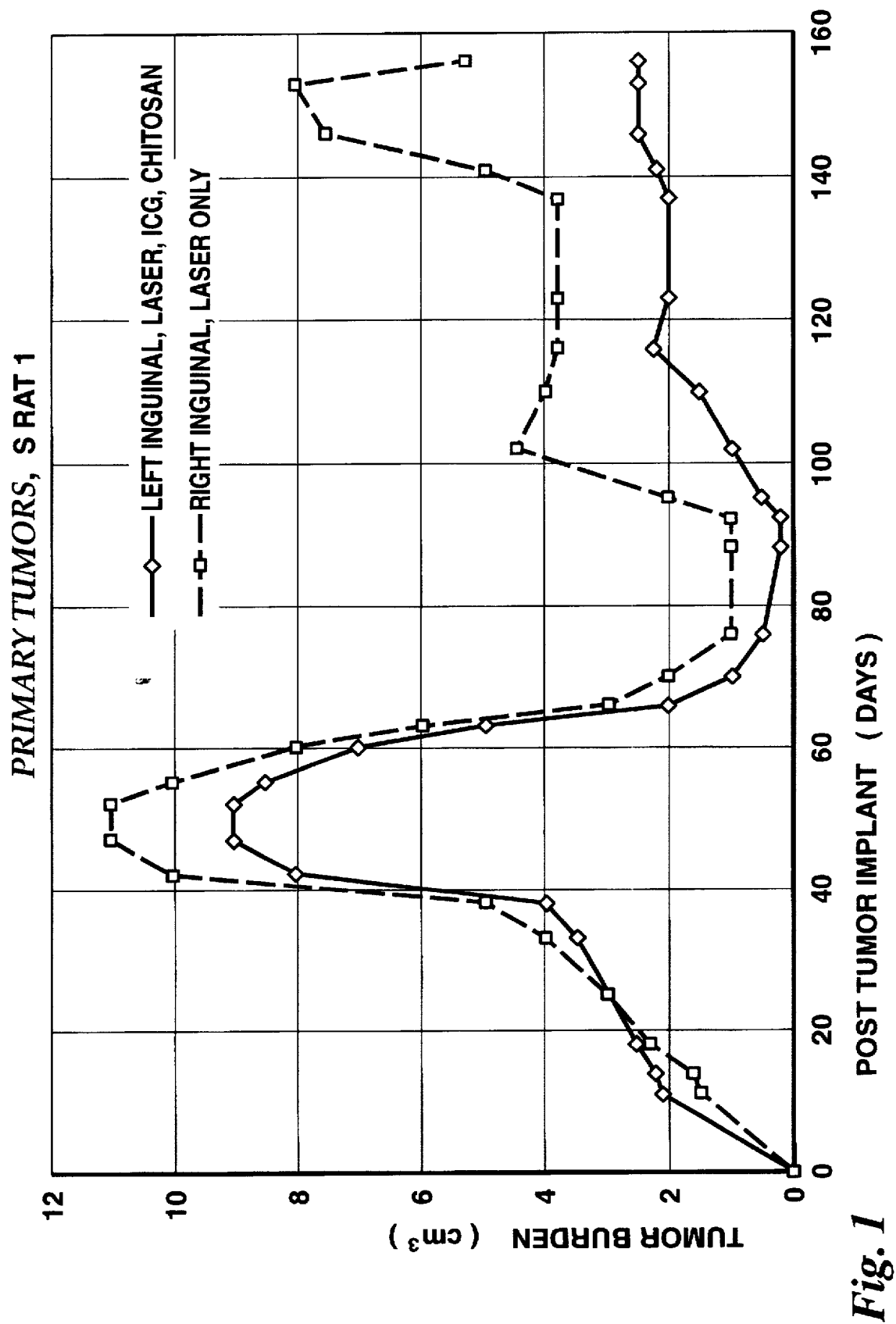
FIG. 1 is a chart related to a study of murine mammary tumors showing tumor burden over time for a particular murine subject whose primary tumor was treated in the manner of the present invention.

The present invention contemplates using chitosan-derived biomaterials, and more particularly, glycated chitosan, in the treatment of neoplasms and other medical disorders. In one example, these biomaterials are used as an immunoadjuvant in a novel cancer treatment. Photodynamic and immunologic therapies are combined by introducing both a chromophore and an chitosan-derived immunoadjuvant (also called immuno-modulator or immunopotentiator) into a neoplasm. Upon application of a laser irradiance sufficient to induce neoplastic cellular destruction, cell-mediated and humoral immune responses to the neoplastic antigens thus released are stimulated (enhanced) by the immunoadjuvant component.

The chromophore and immunoadjuvant are preferably combined into a solution for injection into the center of the tumor mass. It should be recognized however that other methods may be sufficient for localizing the chromophore and immunoadjuvant in the tumor site. One such alternative delivery means is conjugation of the chromophore or immunoadjuvant or both to a tissue specific antibody or tissue specific antigen, such that delivery to the tumor site is enhanced. Any one method, or a combination of varying methods, of localizing the chromophore and immunoadjuvant in the tumor site is acceptable so long as the delivery mechanism insures sufficient concentration of the components in the neoplasm.

CHROMOPHORE

The selection of an appropriate chromophore is largely a matter of coordination with an acceptable laser wavelength of radiation. The wavelength of radiation used must, of course, be complementary to the photoproperties (i.e., absorption peak) of the chromophore. Other chromophore selection criteria include ability to create thermal energy, to evolve singlet oxygen and other active molecules, or to be toxic in their own right such as cis-platinin. In the present invention, the preferred wavelength of radiation is 808±10 nm. The desired chromophores have strong absorption in the red and near-infrared spectral region for which tissue is relatively transparent. Another advantage of this wavelength is that the potential mutagenic effects encountered with UV-excited sensitizers are avoided. Nevertheless, wavelengths of between 150 and 2000 nm may prove effective in individual cases. The preferred chromophore is indocyanine green. Other chromophores may be used, however, their selection being based on desired photophysical and photochemical properties upon which photosensitization efficiency and photocytotoxicity are dependent. Examples of alternative chromophores include, but are not limited to, methylene blue, DHE (polyhaematoporphrin ester/ether), mm-THPP (tetra(meta-hydroxyphenyl)porphyrin), AlPcS$_4$ (aluminium phthalocyanine tetrasulphonate), ZnET2 (zinc aetio-purpurin), and Bchla (bacterio-chlorophyll α).

GLYCATED CHITOSAN

The preferred immunomodulator is chitosan. The presence of primary and secondary alcohol groups, and of primary amino groups in chitosan, facilitate a number of approaches for chemical modifications designed mainly to achieve their solubilization and to impart special properties for specific applications. Their biodegradability and lack of toxicity renders them "biologically friendly," since their degradation products can be utilized for the biosynthesis of glycoconjugate components of living tissues. Chitosan and its derivatives have been utilized for bandages and sutures, burn dressings, skin substitutes, bone and dental prostheses, food packaging, drug encapsulation, cosmetics, metal chelation and associated antioxidant effects, waste water treatment, hemostasis, anticoagulants (after sulfation), and dye doping, among other things.

Solubilization of chitin and chitosan can be achieved by partial hydrolysis to oligosaccharides. For chitosan, treatment with a variety of acids, both organic and inorganic, leads to the formation of water soluble chitosonium salts by protonation of the free amino groups. Additional modifications of the amino groups include the introduction of chemical groups such as carboxymethyl, glyceryl, N-hydroxybutyl and others. Glycation, i.e., non-enzymatic glycosylation of the free amino groups of chitosan, followed by stabilization by reduction, offers a novel approach for the preparation of the chitosan gels and solutions utilized in the present invention.

Glycated chitosan, as indicated above, refers to the products resulting from the reaction between the free amino groups of chitosan and the carbonyl groups of reducing monosaccharides and/or oligosaccharides. The products of this reaction (mainly a mixture of Schiff bases, i.e. the carbon atom of the carbonyl group double bonded to the nitrogen atom of the amino group, and Amadori products, i.e. the carbon atom of said carbonyl group bonded to the nitrogen atom of said amino group by a single bond while an adjacent carbon atom is double bonded to an oxygen atom) may be used as such or after stabilization by reduction with hydrides, such as sodium borohydride, or by exposure to hydrogen in the presence of suitable catalysts. The galactose derivative of chitosan is particularly preferred insofar as it has a relatively higher naturally occurring incidence of its straight chain form. The glycated chitosan may be prepared in a powder form, as a viscous suspension, or in other forms.

One protocol for the preparation of glycated chitosan for use in the present invention is as follows: 3 grams of a reducing monosaccharide (e.g., glucose, galactose, ribose), or an equivalent amount of a reducing oligosaccharide, is dissolved in 100 ml of distilled water under gentle magnetic stirring in an Erlenmeyer flask. One gram of chitosan is added. When the suspension is homogeneous, 0.25 ml of toluene is added, and the flask is sealed with aluminum foil. The magnetic stirring continues for 24 hours at room temperature. After stirring, the suspension is placed in a ventilated fume hood where 1.327 grams of sodium borohydride in 5 ml of 0.1M sodium hydroxide is added to reduce Schiff bases and Amadori products. The solution is then covered loosely with foil, stirred for 10 minutes at room temperature and 50 minutes in an ice bath. After this stirring step, the flask is removed from the ice bath and the solution is acidified to a pH of 5.5 by the dropwise addition of glacial acetic acid (approximately 1.9 ml) under further magnetic stirring to decompose excess borohydride. The solution is then centrifuged for 15 minutes at 15,000 rpm (on a Sorval, rotor SS-34, at 4° C.) in five glass (Corex) centrifuge tubes. The supernatant is decanted and the clear gel layer overlaying the pellets is gently scraped with a steel spatula. Using the supernatant from two of the centrifuge tubes, the pellets are resuspended and recentrifuged in two tubes. Again, the supernatant is decanted and the gel is collected as above. The combined pellets are centrifuged a third time after being resuspended in the supernatant of one tube. The gel is again collected after decanting the supernatant. Pooled gel is then dispersed in pooled supernatant to obtain a homogeneous suspension, which is placed in three dialysis bags (Spectrapor, 25 mm flat width, 12,000–14,000 mol. wt. cut-off). The suspensions are dialyzed overnight at 4° C. against 3.5 gallons of distilled water. The bags are then placed in fresh distilled water and dialysis is continued for an additional 7 hours. After dialysis, the dialysate is removed from the bags and it is homogenized by 3 bursts (10 seconds each) in a Waring blender at high speed. The resulting viscous solution is stored frozen. Before use in the present invention, the frozen material is thawed in a water bath at 370° C., then mixed in a Waring blender to achieve a homogeneous mix.

Alternatively, 100 ml of 1.0% (by weight of chitosan) galactose derivative of chitosan could be prepared as follows:

1. 250 µl of glacial acetic acid is added to 100 ml of pure water and the mixture is stirred.
2. 1.00 grams (by dry weight) of chitosan is added. Stirring continues until all of the chitosan dissolves (there will be a few pieces of insoluble non-chitosan impurities). This will take 1–2 hours.
3. 3.00 grams of galactose is added. Stir and let react for 16 hours or more.
4. It should be noted that hydrogen is produced in this step. While vigorously stirring, a 10% sodium borohydride solution (1.0 gram of sodium borohydride dissolved in 0.1N sodium hydroxide brought to 10.0 ml volume) is added while monitoring the pH and the liquid/foam level in the container. When the pH approaches 6.0, 250 µl of glacial acetic acid is added to lower the pH. The sodium borohydride is added and the pH adjusted until 5.0 ml of the 10% sodium borohydride has been added and the pH is 5.3–5.8. This will require approximately 750 µl of acetic acid and take about 2 hours.
5. The liquid/foam produced is transferred to centrifuge tubes and is centrifuged for 10 minutes at moderate g (approx. 1500) to break up the foam and separate the particulates. Centrifugation is repeated as necessary (½–1 hour).
6. The supernatant liquid is then transferred to dialysis tubing (Spectrapor 1) and dialysis is conducted against 4 liters of pure water for 4 hours.
7. To remove excess water acquired during dialysis, the tubing is placed under an air stream (keeping the membrane moist on the inside) for a period of time (2–6 hours) until the weight is reduced the required amount. (20.4 mm diameter tubing loses approximately 6 g/hour in a fume hood doorway).
8. The dialysis is repeated in 4 liters of water for 6 hours. Then the weight is readjusted in accordance with the previous step.
9. Final dialysis is conducted against 16 liters of pure water for 16 hours, then adjust weight or lyophilize to dryness.

The structure of galacto-chitosan and the preparation of galacto-chitosan from chitosan and D-galactose by reductive amination is shown below.

| Formula | Biopolymer |
|---|---|
Structure of galactochitosan (GC)
Structure
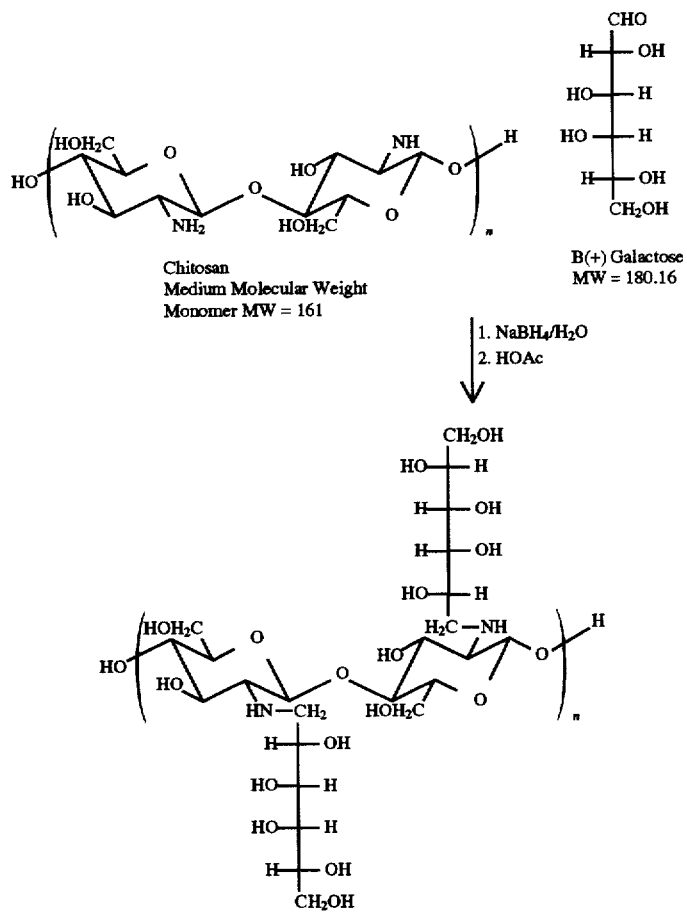
Molecular Weight (approx.): 1.5 million
Preparation of Galactochitosan (GC)
Chitosan
Medium Molecular Weight
Monomer MW = 161
B(+) Galactose
MW = 180.16
1. NaBH₄/H₂O
2. HOAc

USE OF GLYCATED CHITOSAN AS AN IMMUNOADJUVANT

In the preferred embodiment, ICG powder is blended with the glycated chitosan preparation to yield a solution having a concentration of between 0.1% to 2% (0.1 to 2 grams/100 ml) of ICG to glycated chitosan solution. The solution is kept warm until use. The effective dosage of the solution ranges from 70 to 2000 μl. A 100 ml solution of chromophore and glycated chitosan immunoadjuvant also can be prepared from powdered forms of both constituents by added 0.25 grams of ICG and 0.5 grams of glycated chitosan to 100 ml of pure water to yield a useful solution having 0.25% ICG and 0.5% glycated chitosan by weight.

As for laser parameters, a solid state diode laser that emits light in a continuous wave through fiber optics of a diameter between 100 and 2000 μm is preferred, although other lasers may be used, including banks of individual lasers that may or may not all be of the same wavelength. The laser power used can vary between 1 and 60 watts, the preferred power being between 1 and 5 watts. The irradiance duration should last between 1 and 60 minutes, 3 to 6 minutes being favored. The temperature of the lased tumor mass should preferably be raised to about 140° F. or 60° C.

In the most preferred embodiment, a solution of ICG and glycated chitosan is prepared as described above at a concentration of 0.25 to 2% of ICG to chitosan. The solution is injected into the center of the neoplasm at a dosage of 70 to 400 μl. The neoplasm is then lased using a laser having a power of about 5 watts and a wavelength of radiation capable of readily penetrating normal cellular tissues without significant disruption. The irradiation continues for a duration of 1 to 10 minutes, which is sufficient to elevate the temperature of the neoplasm to a level that induces neoplastic cellular destruction and liberates tumor antigens which stimulate cell-mediated and humoral immune responses.

OTHER USES FOR GLYCATED CHITOSAN AND DERIVATIVES THEREOF

Other medical and industrial uses for glycated chitosan are anticipated. In addition to its use as an immunoadjuvant or a component thereof in combination with sensitizing dyes and laser/sensitizer assisted immunotherapy, glycated chitosan might be used to facilitate the application of sodium fluoride to the surface of teeth prior to fusion onto the enamel by laser irradiation. It might also be used to prepare suspensions of hydroxyapatite and other formulations of calcium phosphate utilized for bone and dental prosthesis. Another use would be as a component of skin substitutes, sutures, dressings and bandages for burns, wounds and surgical procedures.

A further use of glycated chitosan, alone or in combination with other drugs, might be as an antiinfection treatment in septicemia, antibiotic resistance, or antibiotic intolerance. It might also be used in cosmetic and pharmaceutical formulations, creams, salves, etc.

A still further use would be as an immunostimulant in the treatment of immuno-compromised patients including but not limited to cancer and acquired immunodeficiency syndrome. This includes, but is not limited to, the use of chitosan derivatives with side chains derived from tumors and microorganisms.

Gel and soluble forms of glycated chitosan will be used individually or in combination, both as such and/or after additional chemical or enzymatic modification. These modifications include, but are not limited to, the generation of reactive groups such as carbonyls and carboxyl groups on the substituents introduced by glycation.

Aldehydes will be generated by oxidation of the carbohydrate side chain (e.g. treatment with periodate or lead tetraaceate) or, for example, the enzymatic oxidation of the primary alcohol group of galactosyl residues with galactosyl oxidase.

Oxidation of the aldehyde groups (e.g. by treatment with hypohalites) will be utilized to obtain the carboxylic acid derivatives. Alternatively, bifunctional compounds containing both free carbonyl and carboxylic groups (.g. uronic acids) will be utilized during the glycation reaction.

Chitosan deamination with nitrous acid generates reducing aldoses and oligosaccharides suitable for the glycation of chitosan. Deamination of the deacetylated glucosaminyl residues by nitrous acid results in the selective cleavage of their glycosidic bonds with the formation of 2,5-anhydro-D-mannose residues. Depending on the composition of specific areas of the chitosan chain, the anhydro hexose could be released as the monosaccharide, or occupy the reducing end of an oligosaccharide. Release of free N-acetylglucosamine could also occur from some regions of the chitosan chain. Similar treatment of N-deacetylated glycoproteins and glycolipids can be utilized to obtain oligosaccharides of defined chemical composition and biological activity for special preparations of glycated chitosan. This includes normal as well as pathological glycoconjugates.

The various products obtained by chitosan glycation will be utilized as such or reacted with other natural or synthetic materials, e.g., reaction of aldehyde-containing derivatives of glycated chitosan with substances containing two or more free amino groups, such as on the side chains of amino acids rich in lysine residues as in collagen, on hexosamine residues as in chitosan and deacetylated glycoconjugates, or on natural and synthetic diamines and polyamines. This is expected to generate crosslinking through Schiff base formation and subsequent rearrangements, condensation, dehydration, etc.

Stabilization of modified glycated chitosan materials can be made by chemical reduction or by curing involving rearrangements, condensation or dehydration, either spontaneous or by incubation under various conditions of temperature, humidity and pressure.

The chemistry of Amadori reaarangements, Schiff bases and the Leukart-Wallach reaction is detailed in *The Merck Index*, Ninth Edition (1976) pp. ONR-3, ONR-55 and ONR-80, Library of Congress Card No. 76-27231, the same being incorporated herein by reference. The chemistry of nucleophilic addition reactions as applicable to the present invention is detailed in Chapter 19 of Morrison and Boyd, *Organic Chemistry*, Second Edition (eighth printing 1970), Library of Congress Card No. 66-25695, the same being incorporated herein by reference.

EXPERIMENTAL STUDIES

Further description of laser/sensitizer assisted immunotherapy utilizing a chitosan-derived immunoadjuvant, including components, parameters and procedures, is contained in the following summary of a study of murine mammary tumors.

A. Materials and Methods

1. The Laser

A diode laser was used in this study. The Industrial Semiconductor Laser ISL50F (McDonnell Douglas Aerospace, St. Louis, Mo.), employs a diode array that is electrically powered by a diode driver. The laser emits radiation at wavelength of 808±10 nm, either in pulsed or in continuous mode. Its maximum near infrared power in the available configuration output is 35 watts. The laser is operated with standard electric power (110/120 VAC). A microprocessor monitors and adjusts the laser operating parameters. Laser energy can be delivered through optical fibers of various sizes. A red laser diode emits 670 nm light at 0.9 mW as the aiming beam. The continuous wave mode was employed in this experiment.

In the experiment, different power and duration of laser irradiation, ranging from 3 minutes at 5 watts to 5 minutes at 15 watts, were used. The output power was measured before, during and after the procedure using a Joule/Watt meter (Ophir Optics, Israel). Two types of fiber optics were used: 600 µm and 1200 µm in diameter.

2. The Preparation of Animals

Wistar Furth female rats, age 6 to 7 weeks and weighing 100 to 125 grams, were chosen for the study. The model is a metastatic transplantable rat mammary tumor. The tumor strain was the DMBA-4. Tumor cells (about 25,000 cells) were transplanted to the rats by injection into the superficial inguinal area between the skin and the muscle layer. Certain selected rats were injected with tumor cells in both left and right inguinal areas for simultaneous tumor growth.

The rats were fed a special food, a high saturated fat diet, to facilitate the growth of the tumor. The tumor usually grew to about 1 to 4 cm³ within 10 to 14 days of tumor transplantation. In most cases the rat tumors were treated before they grew beyond 5 cm³.

Before laser treatment, anesthesia was applied (100 µl xylazine and ketamine solution IM) and the hair overlaying the tumor was clipped and shaved. After the treatment, the rats were maintained in separate cages and still fed with the same high fat diet. The rats were observed daily and the morphological measurements of tumors—both laser treated and untreated controls—were made twice a week.

3. Sensitizer Administration

The sensitizer indocyanine green (ICG) (Sigma Chemical Co., St. Louis) was used in two forms: ICG in water and ICG in glycated chitosan, the concentration being 0.5% and 1% (g/100 ml) ICG to water or chitosan. In the case of chitosan solution, an ICG powder was mixed with glycated chitosan made as hereinabove described, after the gel was brought to 37° C. from frozen state (−4° C.), in a glass grinder to obtain a uniform solution. The sensitizer solution then was injected into the center of the targeted tumor, either 24 hours prior to laser treatment or just 10 minutes before the procedure. The dosage varied between 70 µl to 400 µl to one tumor.

For the rats with transplanted primary tumors in both inguinal areas, only one tumor received the ICG-Chitosan injection. However both tumors were treated using the same laser parameters.

4. Laser Treatment

The laser energy was delivered to the treatment sites through fibers having diameters of 600 or 1200 µm. The tip of the fiber was maintained 4 mm from the skin. The fiber tip was moved evenly and slowly through all sides of the tumor to ensure a uniform energy distribution. A thin water film (20° C.) was constantly applied on the surface of treatment sites to prevent unnecessary damage of skin due to the surface heat build up.

For the rats with two simultaneous primary tumors, one tumor was lased with the aid of ICG-Chitosan and the other was treated by the laser only. Fifty-six rats were treated using various laser parameters in conjunction with ICG-Chitosan solutions. Sixteen rats were injected with 100–200 µl of a 1% ICG-H₂O solution and lased with various irradiances from 3–5 minutes and from 3–10 watts.

B. Results

1. The Survival Rates

In total, one hundred five (105) rats were used in the study up to Apr. 1, 1995. All the rats were injected with the metastatic transplantable rat mammary tumor cells, either in one inguinal region or both. The rats were divided into three groups: (1) control, (2) laser treated with ICG-H₂O solution, and (3) laser treated with ICG-Chitosan solution. The survival rates of the various grouped subjects are summarized on Table I.

TABLE I

The Survival Rate of Rats with Tumor Transplant

| Group | Survival Days | Number of Rats |
|---|---|---|
| Control | 32.4 ± 3.6 | 13 |
| Laser Treated with ICG only | 29.0 ± 3.5 | 7 |
| Laser Treated with ICG-Chitosan | 42.7 ± 28.9 | 55 |
| ICG-Chitosan Treated (w/o long survival rats) | 32.9 ± 5.7 | 49 |
| ICG-Chitosan Treated (long survival rats only)* | 114.3 ± 39.8 | 6 |
| ICG-Chitosan Treated 5w @ 3 to 6 mins (w/o long survival rats)** | 33.6 ± 6.0 | 36 |
| ICG-Chitosan Treated 5w @ 3 to 6 mins (with long survival rats) | 45.4 ± 32.4 | 42 |

*Out of the six long term survival rats, three are still alive. The data collected in this table were up to January 16, 1995.
**The six long survival rats were treated using this laser power and the duration range (see Table II for more detail).

The average survival time for the 33 control rats was 31.5 days after the tumor transplant; the average was 29.0 days for laser treated rats injected with aqueous ICG only; the overall average survival time was 45.6 days for the ICG-Chitosan injected laser treated rats. Among the 56 rats in the last group, six rats achieved long term survival (at least twice that of the control rats), without which the group survival rate would be 32.8 days. On the other hand, the six rats gave rise to an average 152.0 days of survival. It is worthwhile to note that three rats, Srat3, Srat4 and Srat6, were still alive when the report was written after they have survived 220, 192 and 147 days, respectively, up to Apr. 1, 1995.

2. The Tumor Responses to Laser Treatment

Table I shows that tumor rats in both group 2 and group 3 responded positively to laser energy. Almost all the tumors had temperature elevation immediately after the laser treatment. The ICG-H₂O or ICG-Chitosan solution injected tumors usually raised temperature by 40° F., while the ICG free tumor still raised temperature but at a lower level, usually 20° to 300° F. above the body temperature depending on the laser power and duration.

Internal explosions often occurred during the procedure due to the sudden temperature increase. It was more evident under high laser power, above 10 watts for example. High power produced skin damage in most cases, even with constant application of water droplets on the treatment surface.

The tumor cell destruction under high laser power (10–15 W) was rather superficial and deeper tumor cells often survived the laser assault. Better results were obtained when lower laser powers were applied. All the six long term survival rats resulted from the 5 watt treatment (4 rats with 3 minute exposure times and 2 rats with 5 minutes). See Table II.

aggressive than Srat2. Note the bigger burden on the right inguinal in both cases (no ICG-Chitosan injection).

TABLE II

Parameters for Laser-ICG-Chitosan Treated Long Term Survival Rats

| Animal Rat Number | Tumor Transplant | | ICG-Chitosan Administration | | | Laser Treatment* | | Survival Post Tumor Transplant |
|---|---|---|---|---|---|---|---|---|
| | Date | Locations | Time Prior to Treatment | Dosage | Location | Date | Power (Watts) | Duration (minutes) | (Days) |
| Srat1 Rat #5/3-29-94 | 3-18-94 | Both Legs | 24 hours | 70 μl @ 1% | Left Leg | 3-29-94 | 5.00 | 3 | 156 |
| Srat2 Rat #1/6-3-94 | 5-23-94 | Both Legs | 24 hours | 70 μl @ 1% | Left Leg | 6-3-94 | 5.00 | 3 | 125 |
| Srat3 Rat #5/9-1-94 | 8-19-94 | Left Leg | 24 hours | 150 μl @ 0.5% | Left Leg | 9-1-94 | 5.06 | 6 | 150** as of 1/16/94 |
| Srat4 Rat #2/9-27-94 | 9-16-94 | Both Legs | 24 hours | 100 μl @ 1% | Right Leg | 9-27-98 | 5.20 | 5 | 120** as of 1/16/94 |
| Srat5 Rat #3/11-8-94 | 10-31-94 | Left Leg | 10 minutes | 150 μl @ 0.5% | Left Leg | 11-8-94 | 4.95 | 3 | z65 |
| Srat6 Rat #4/11-11-94 | 10-31-94 | Left Leg | 10 minutes | 100 μl @ 0.5% | Left Leg | 11-11-94 | 5.12 | 3 | 80** as of 1/16/94 |

*Totally 42 rats wre treated using parameters in this range, resulting in a 14% survival rate.
**Rat is still alive.

In total, 43 rats were treated with laser power of 5 watts and an irradiation duration of 3 to 6 minutes; this gives rise to a 14% long term survival rate in this group. Under these parameters, without the six long survival rats, the average survival reached 32.8±6.3 days.

Immediately after laser treatment, all the tumors showed a slower growth within the first few days, then returned to a normal growth rate. Often the tumors would be partially bitten or chewed, but that would not stop or slow the tumor growth. Most rats died around 30 to 35 days except for the rats listed in Table II. About half the treated rats later developed secondary tumors, most as "hand bags" (metastatic to lymph nodes in the axillary region); the local expansions around the primary tumors were also in lymph nodes. In either case, the secondary tumors continued to grow until death occurred, except for the rats in Table II.

3. Tumor Development of the Long Term Survival Rats

All six rats in Table II were treated using 5 watts power with either three minutes duration (four rats) or five minutes (two rats). More importantly, all of them were injected with ICG-Chitosan gel solution. For rats with two transplanted primary tumors, only one of the two tumors received the ICG-Chitosan solution and the other was lased without any ICG sensitizer. For rats with only one primary tumor, the ICG-Chitosan was used. The ICG-Chitosan solution was 0.5% to 1% and the dosage varied from 70 μl to 150 μl per tumor. The ICG-Chitosan was usually injected directly into the tumor either 24 hours or 10 minutes before the laser treatment.

Figure 2:
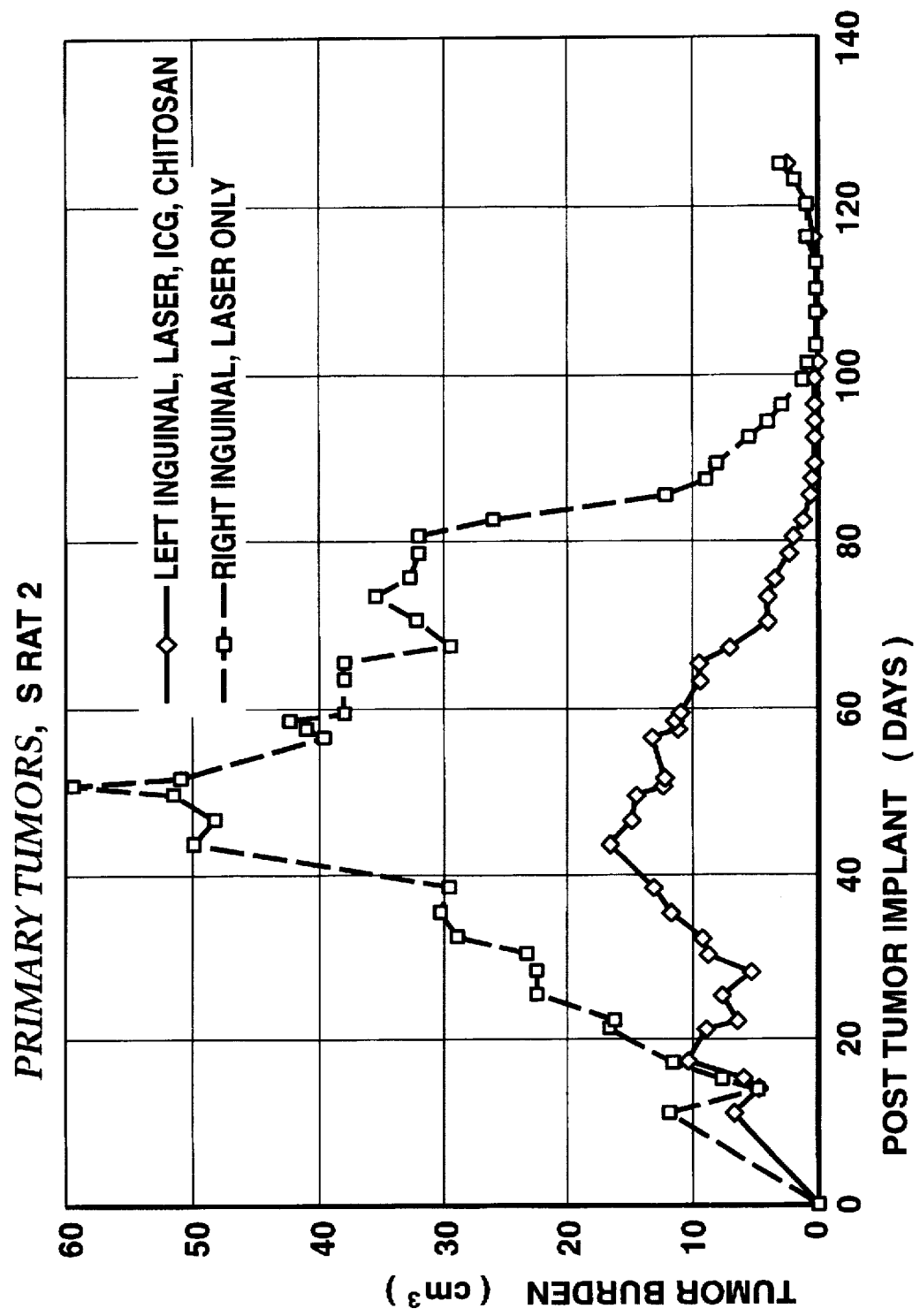
FIG. 2 is a chart similar to FIG. 1 for a second treated murine subject.
Figure 3:
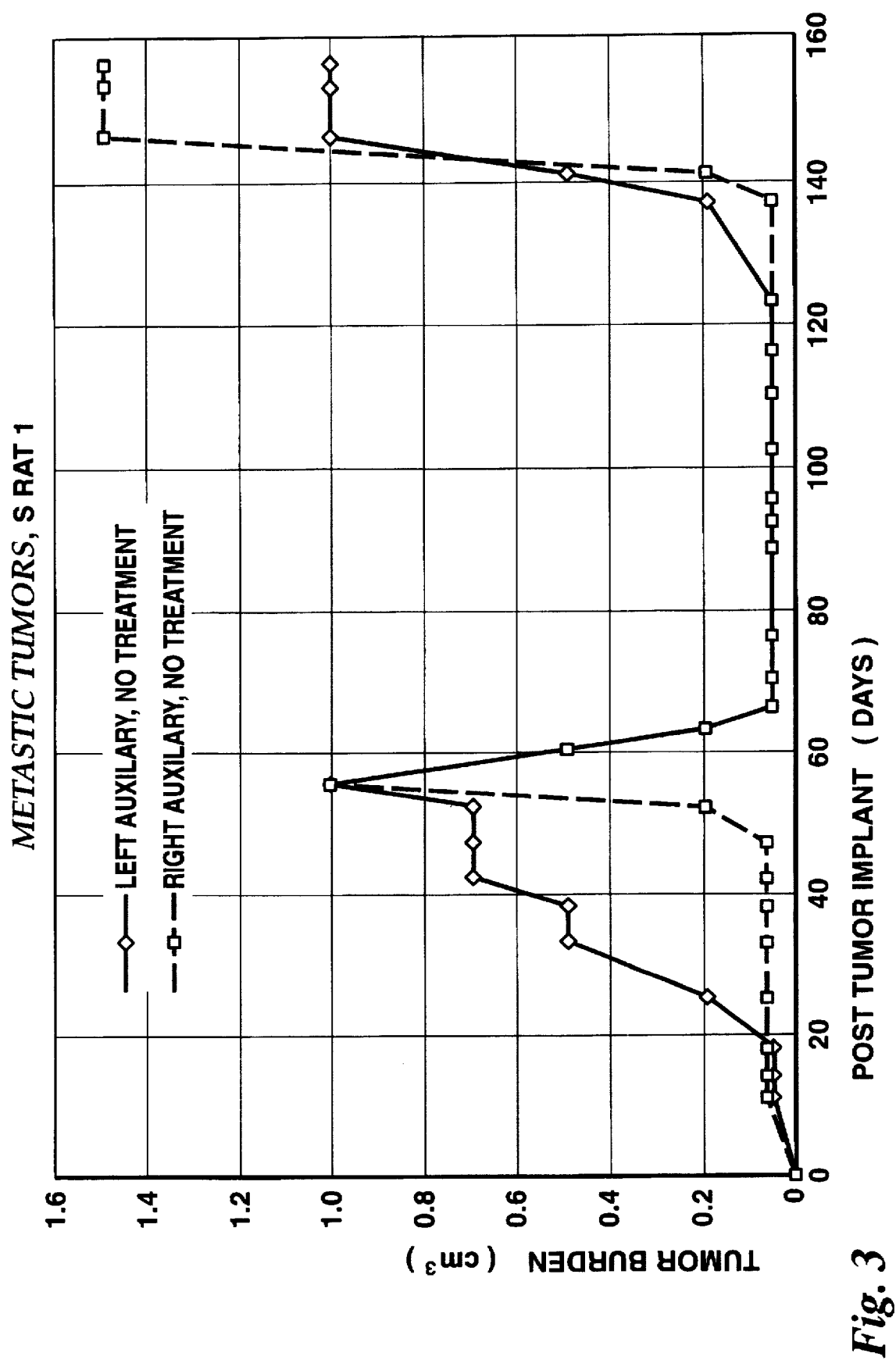
FIG. 3 is a chart showing tumor burden over time for untreated secondary tumors in the murine subject of FIG. 1.
Figure 4:
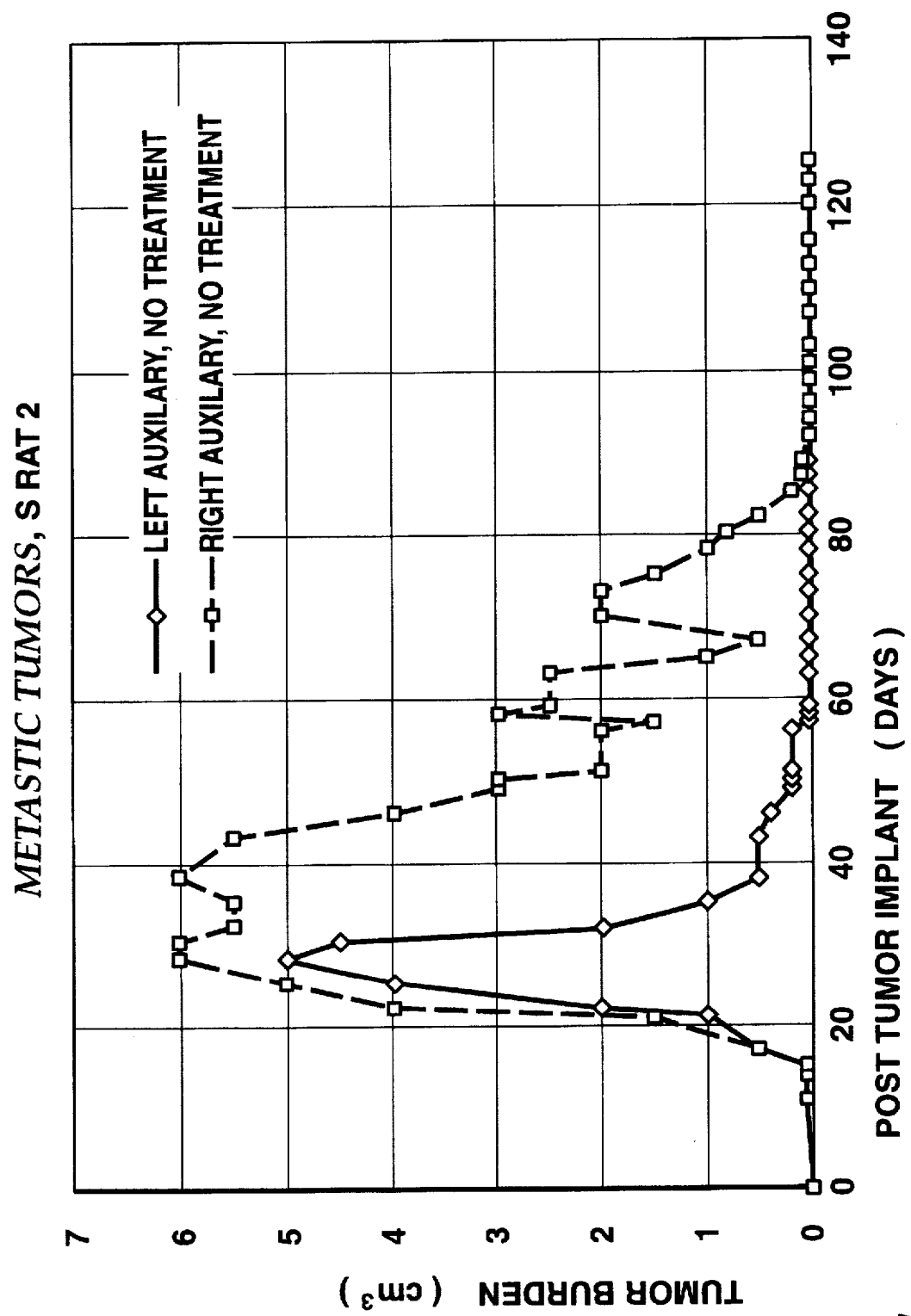
FIG. 4 is a chart showing tumor burden over time for untreated secondary tumors in the murine subject of FIG. 2.

Like all the other rats, the tumors continued to grow after treatment, and most of the tumors metastasized along the milk line to the axillary nodes and the opposite inguinal nodes. However, the development of tumors took a dramatic turn at a later stage. Shown in FIGS. 1 and 2 are the growth charts of the primary tumors of Srat1 and Srat2, treated by laser; the left inguinal tumor was injected with ICG-Chitosan and the right inguinal tumors were not. The growth reached a peak around 50 days after the tumor transplant, and then started to regress. The tumors continued to shrink and reached their minimum size around 90 days. Afterwards the tumors started growing again, with Srat1 being more The secondary tumors of Srat1 and Srat2 appeared around day 20 after tumor transplant, and went through the same pattern as the primaries—growth/shrinkage/growth, as shown in FIGS. 3 and 4. In the case of Srat2, the recurrence of secondary tumors was almost negligible.

Figure 5:
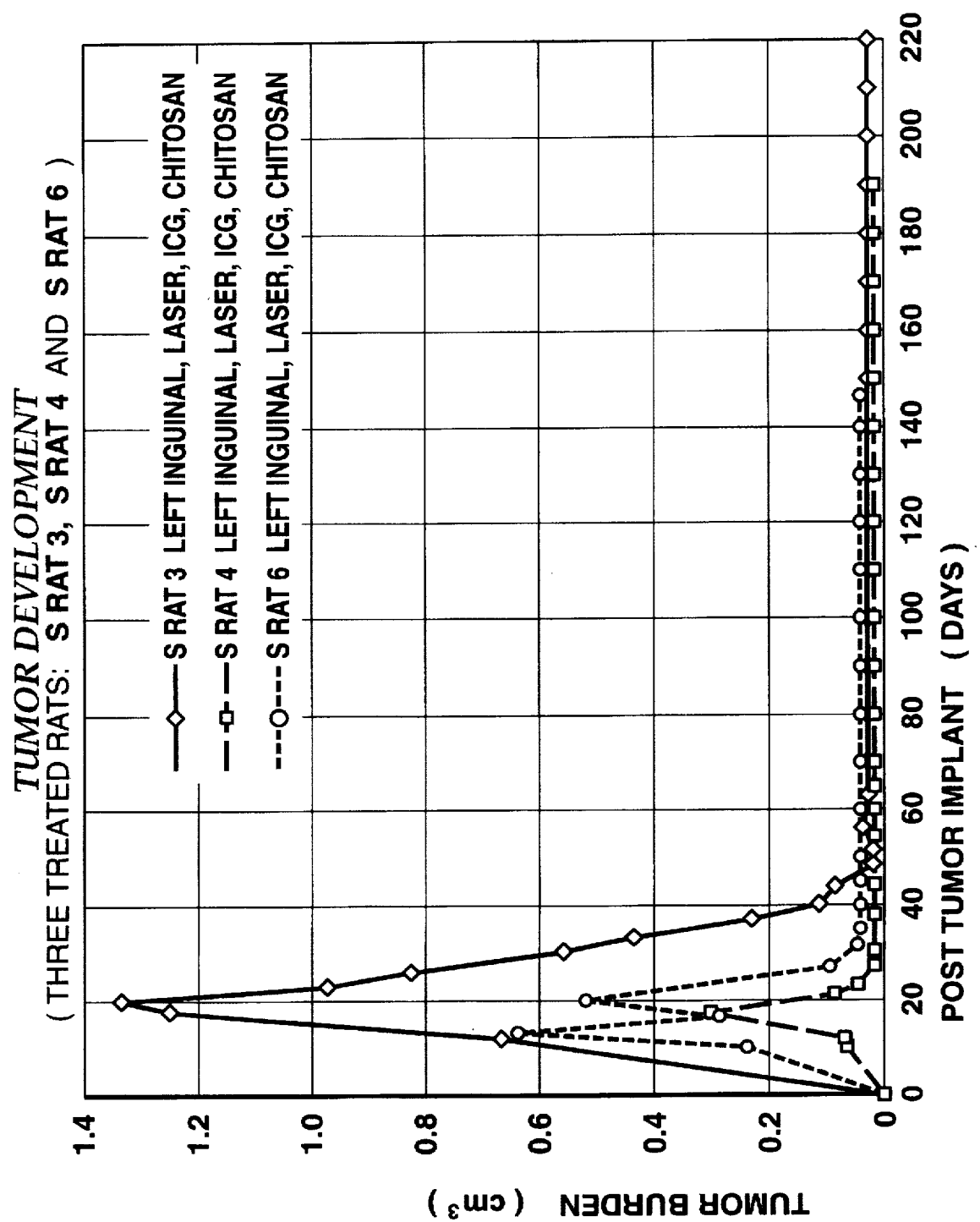
FIG. 5 is a chart showing tumor burden over time for three other treated murine subjects.

The tumor growth of three other rats is shown in FIG. 5. Srat3 and Srat6 started with only one primary tumor and Srat4 with two. FIG. 5 shows a much earlier response: tumor reduction started around 20 to 25 days. Furthermore, there are so far no secondary tumors, and the primary tumors have become only a small hard core of fibrous tissue; just a remnant of the tumor. Further development will be observed since all three remain alive at this time (Apr. 1, 1995).

4. Improvement of the Experiment

Early experiments had been mainly focused on establishing workable conditions, including laser parameters, as well as the concentration and dosage of ICG-Chitosan. No long term survival was observed in the first few groups. Suggested by in vitro and in vivo results, work had been proceeding in the laser power range of 3 to 5 watts. ICG-Chitosan solution between 0.5% to 1% seem to be effective. A steady long term survival rate of 10% has been achieved, and even a 20% rate in one of the recent rat groups.

C. Discussion

Clearly, the photothermal effect of the 808 nm diode laser on organized tissue can be greatly enhanced when the chromophore ICG with an absorption peak around 800 nm is used. The 808 nm laser energy can penetrate readily through the normal tissue leaving the cellular structure largely intact within regulated power ranges.

It is the ICG molecule, when injected to the target tissue, that absorbs strongly the 808 nm radiation and reaches an excited state. When the molecule returns to ground state, the stored energy is released in the form of heat which can be absorbed by surrounding tissue to elevate temperature. (The excited ICG molecule may also cause other biochemical reactions which may be the key in our induced immunological responses.) When a sufficient amount of ICG molecules are excited within a certain time (normally shorter than the tissue thermal relaxation time), the released heat can be absorbed by tissue cells faster than it can be dispersed. If the exposure to laser is long enough, the accumulated heat energy can raise tissue temperature to a level at which photothermal destruction of organized tissue can occur. This destruction can be achieved with certain selected laser powers and irradiation durations. It appears that a laser power around 3 to 5 watts is sufficient to cause fatal injury to tumor cells.

Higher powers, in conjunction with ICG, can cause quick and more drastic thermal injury to the tissue, but some undesirable results may arise. The high power irradiation gives rise to a much faster temperature build-up, often leading to internal explosions and quick tissue carbonization, particularly on the treatment surface when oxygen is abundant in the air. A surface cooling procedure, either by water film or by helium gas may not be able to slow down the carbonization, which changes the surface tissue properties from almost transparent to highly absorbent to the 808 nm wavelength. The 808 nm radiation would be in turn absorbed further by the carbonized tissue. This would impede the penetration of the laser energy, resulting in a superficial and limited spatial thermal destruction of intended malignant tissue.

The thermal impact alone may slow down the short term tumor growth, but may not alter the predestined fate for hosts who have acquired tumors. As shown in Table I, the second group, treated by laser with the aid of ICG-$H_2O$ solution, did not show any improvement on the survival rate. Of course, the destruction of tumor cells due to photothermal interaction was a predominant effect. However, due to the aggressive nature of the tumors, total eradication was rarely achieved by the thermal destruction alone; just as in the cases of surgical removal and radiation therapy.

CONCLUSION

It is thus apparent that other mechanisms must be utilized in order to deal with the root cause of the malignant cell multiplication. The ideal mechanism, of course, is the self-immunological defense system, which can prevent growth of abnormal cells. It is when the natural immune functions are debilitated, or not adequate in response to foreign element invasion, that cancers occur. If natural immune defense failed to stop the uncontrolled growth of cells, endogenous or exogenous, stimulated immune responses are needed. As previously stated, it has long been known that certain chemicals may enhance the natural defense mechanism, but often the enhancement is one or several steps behind the tumor growth. The model described herein was directed to a combined PDT and immunotherapeutic treatment.

Other modalities, such as chemotherapy and radiation therapy, often kill cells indiscriminately so that the collateral damage can be just as fatal. And though PDT relies on heat and/or toxic singlet oxygen generated by treatment of laser and certain photosensitizers to kill tumor cells, it still is not a means to affect the host's self-immunological defense system. By using a combination of laser, chromophore, and immunomodulator, the present invention provides a novel cancer treatment.

The effect of this invention in stimulating cell-mediated and humoral immune responses in the host is shown FIGS. 1–5. The growth charts (FIGS. 1 and 2) show the change of the tumor burden. Fifty days after tumor transplantation (40 days after laser-ICG-Chitosan treatment), primary tumors reached their maximum sizes. The reduction of tumor growth and size afterwards can only be explained by the generated immunological response, since only the self-defense mechanism, when fully developed, would slow down and stop the tumor growth, and the disfunctioning tumor cells would be engulfed by macrophages. Without this exotic feature, none of the rats could have survived over 35 or 40 days, as demonstrated by the first two groups of experimental rats in Table I.

The ICG-Chitosan injected tumor (left inguinal in most cases of the six rats in Table II) had a slower growth rate, a sign of a more direct impact of the immunoadjuvant, even though both tumors were treated with same laser power and duration. The ICG-Chitosan injected tumor in general responded more to the laser treatment. The thermal interaction alone, in conjunction with ICG, had effectively reduced the tumor burden on a large scale. The chitosan apparently added the immunological stimulation. The combination of the thermal and immunological effects appear to be the explanation as to why the left inguinal tumors had less growth than those of the right as shown in FIGS. 1 and 2.

The generation and acceleration of the immunological defense system response is further supported by the evolution of the secondary tumors of the long surviving rats. The metastasis usually occurred to half the rats around 15 to 20 days after the transplantation of primary tumors. The secondary tumors appeared in most cases along the milk lines and continued to grow until death. However, the metastatic tumors of Srat1 and Srat2 in FIGS. 3 and 4 showed exactly the same trend as in the primaries (FIGS. 1 and 2), with neither ICG-Chitosan injection nor laser treatment. FIG. 5 depicts the growth of primary tumors of three rats (Srat3, Srat4 and Srat6), all of them following the same development—growth/treatment/growth/ reduction. Furthermore, these three rats developed their full responses earlier; the tumor growth was stopped around 20 to 25 days after tumor transplantation and secondary tumors never appeared. This early establishment of the induced immunological defense mechanism may explain why these rats are still alive and have no signs of tumor recurrence.

In conclusion, long term survival with total cancer eradication can be achieved by laser-chromophore-adjuvant induced immunological responses. It is a combined result of reduced tumor burden due to photothermal interactions and an enhanced immune system response due to the addition of chitosan or other immunomodulators. The experimental results have been improving constantly. The first few groups yielded no long term survivors whereas a steady 10% long term survival rate is now achieved. Within the current adapted laser power (5 watts) and the irradiation duration (3 to 6 minutes), the long term survival rate reaches up to 14%

While the invention has been described with a certain degree of particularity, it is manifest that many changes may be made in the method hereinabove described without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An immunoadjuvant comprising a suspension or a solution of glycated chitosan.

2. The immunoadjuvant according to claim 1, further comprising a chromophore.

3. The immunoadvant according to claim 2, wherein said chromophore is selected from the group consisting of indocyanine green, methylene blue, DHE, m-THPP, AlPcS$_4$, ZnET2, and Bchla.

4. The immunoadjuvant according to claim 2, wherein said chromophore is indocyanine green.

5. The immunoadjuvant according to claim 2, wherein said immunoadjuvant comprises a solution.

6. The immunoadjuvant according to claim 5, said solution comprising 0.25% by weight of said chromophore and 0.5% by weight of said glycated chitosan.

7. The immunoadjuvant according to claim 1, said immunoadjuvant further comprising a tumor specific antibody conjugated to said glycated chitosan.

8. The immunoadjuvant according to claim 1, said immunoadjuvant further comprising a tumor specific antigen conjugated to said glycated chitosan.

9. The immunoadjuvant according to claim 1, wherein said glycated chitosan includes a carbonyl or carboxyl reactive group.

10. An immunoadjuvant consisting essentially of glycated chitosan.

11. A chitosan-derived biomaterial comprising a linear homopolymer of deacetylated chitin (chitosan), said deacetylated chitin having a number of otherwise free amino groups bonded to a carbonyl group of a reducing monosaccharide or oligosaccharide to form glycated chitosan.

12. The chitosan-derived biomaterial according to claim 11, wherein said glycated chitosan is in the form of a Schiff base.

13. The chitosan-derived biomaterial according to claim 11, wherein said glycated chitosan is in the form of an Amadori product.

14. The chitosan-derived biomaterial according to claim 11, wherein said glycated chitosan is in the form of a reduced Schiff base.

15. The chitosan-derived biomaterial according to claim 11, wherein said monosaccharide is galactose.

16. The chitosan-derived biomaterial according to claim 11, wherein said glycated chitosan includes a carbonyl or carboxyl reactive group.

17. A composition for use in conditioning a neoplasm for tandem photophysical and immunologic treatment, comprising a combination of a chromophore and an immunoadjuvant, wherein the chromophore and the immunoadjuvant are conjugated to a tumor specific antigen, and wherein the immunoadjuvant is glycated chitosan.

18. A composition for use in conditioning a neoplasm for tandem photophysical and immunologic treatment, comprising a combination of a chromophore and an immunoadjuvant, wherein the chromophore and the immunoadjuvant are conjugated to a tumor specific antibody, and wherein the immunoadjuvant is glycated chitosan.

19. An injectable solution for conditioning a neoplasm for tandem photophysical and immunologic treatment comprising a mixture of a chromophore and an immunoadjuvant wherein the immunoadjuvant is glycated chitosan.

* * * * *